United States Patent
Discenzo

(10) Patent No.: US 7,134,323 B1
(45) Date of Patent: Nov. 14, 2006

(54) SYSTEM AND METHOD FOR DYNAMIC LUBRICATION ADJUSTMENT FOR A LUBRICATION ANALYSIS SYSTEM

(75) Inventor: Frederick M. Discenzo, Brecksville, OH (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 11 days.

(21) Appl. No.: 11/041,317

(22) Filed: Jan. 24, 2005

Related U.S. Application Data

(63) Continuation of application No. 10/370,866, filed on Feb. 20, 2003, now Pat. No. 6,877,360, which is a continuation of application No. 10/036,154, filed on Oct. 22, 2001, now Pat. No. 6,546,785, which is a continuation-in-part of application No. 09/257,680, filed on Feb. 25, 1999, now Pat. No. 6,324,899, which is a continuation-in-part of application No. 09/054,117, filed on Apr. 2, 1998, now Pat. No. 6,023,961.

(51) Int. Cl.
G01N 33/26 (2006.01)
F01M 1/18 (2006.01)

(52) U.S. Cl. .............. 73/53.05; 184/6.4; 702/34; 702/81; 702/183

(58) Field of Classification Search .............. 73/53.01, 73/53.04, 53.05, 54.01, 54.02, 61.41, 61.42; 702/33, 34, 81, 82, 130, 136, 183, 184; 184/6.4
See application file for complete search history.

(56) References Cited

U.S. PATENT DOCUMENTS

| | | | |
|---|---|---|---|
| 1,996,063 A | 4/1935 | Corkran | |
| 2,883,855 A | 4/1959 | Spengler et al. | |
| 3,785,196 A | 1/1974 | Smith | |
| 3,968,741 A * | 7/1976 | Hunt | 99/330 |
| 4,167,925 A | 9/1979 | Hosaka et al. | |
| 4,675,662 A | 6/1987 | Kondo et al. | |
| 4,677,847 A | 7/1987 | Sawatari et al. | |
| 4,757,878 A | 7/1988 | Iino et al. | |
| 4,782,332 A | 11/1988 | Cipris et al. | |
| 4,792,791 A | 12/1988 | Cipris et al. | |
| 4,847,768 A | 7/1989 | Schwartz et al. | |
| 4,854,159 A | 8/1989 | Bates | |
| 4,922,745 A | 5/1990 | Rudkin et al. | |
| 5,038,893 A | 8/1991 | Willner et al. | |
| 5,049,742 A * | 9/1991 | Hosonuma et al. | 250/301 |

(Continued)

FOREIGN PATENT DOCUMENTS

EP 1008837 A1 6/2000

(Continued)

OTHER PUBLICATIONS

Saloka et al., "A Capacitive Oil Deterioration Sensor", SAE Paper No. 910497, pp. 137-146.*

(Continued)

*Primary Examiner*—Hezron Williams
*Assistant Examiner*—David A. Rogers
(74) *Attorney, Agent, or Firm*—Amin, Turocy & Calvin LLP; Alexander R. Kuszewski

(57) ABSTRACT

A system and methodology is provided for dynamically adjusting fluids that operate as a lubricant in a machine. The system includes a control module having a processor and one or more sensors providing data to the processor in situ with the machine, wherein the processor employs the data to monitor the fluid. One or more inputs are provided to receive a plurality of additives that are associated with the fluid, wherein actuators are employed by the processor to dispense the additives to the fluid. The processor dispenses the fluid based upon one or more parameters of the fluid.

9 Claims, 11 Drawing Sheets

U.S. PATENT DOCUMENTS

| | | |
|---|---|---|
| 5,067,455 A | 11/1991 | Okajima et al. |
| 5,132,225 A | 7/1992 | Dickakian |
| 5,177,696 A | 1/1993 | Bonne |
| 5,184,505 A | 2/1993 | van den Berg |
| 5,200,027 A | 4/1993 | Lee et al. |
| 5,275,258 A | 1/1994 | Bousseau |
| 5,435,170 A * | 7/1995 | Voelker et al. ............ 73/53.05 |
| 5,487,313 A | 1/1996 | Johnson |
| 5,487,491 A | 1/1996 | Smith et al. |
| 5,514,968 A | 5/1996 | Spanjers |
| 5,528,899 A | 6/1996 | Ono |
| 5,540,086 A | 7/1996 | Park et al. |
| 5,571,950 A | 11/1996 | Waddoups et al. |
| 5,614,830 A | 3/1997 | Dickert et al. |
| 5,660,728 A | 8/1997 | Saaski et al. |
| 5,747,667 A | 5/1998 | Sadar |
| 5,777,211 A | 7/1998 | Binienda et al. |
| 5,789,665 A | 8/1998 | Voelker et al. |
| 5,817,928 A | 10/1998 | Garvey, III et al. |
| 5,821,399 A | 10/1998 | Zelin |
| 5,887,978 A | 3/1999 | Lunghofer et al. |
| 5,889,211 A | 3/1999 | Maudie et al. |
| 5,950,147 A | 9/1999 | Sarangapani et al. |
| 5,959,188 A | 9/1999 | Deutsch et al. |
| 5,968,371 A | 10/1999 | Verdegan et al. |
| 5,996,337 A | 12/1999 | Blosser et al. |
| 6,002,248 A | 12/1999 | Binder |
| 6,023,961 A | 2/2000 | Discenzo et al. |
| 6,029,495 A | 2/2000 | Munetaka |
| 6,117,001 A | 9/2000 | Enomoto et al. |
| 6,210,326 B1 | 4/2001 | Ehwald |
| 6,324,899 B1 | 12/2001 | Discenzo |
| 6,389,874 B1 | 5/2002 | Huff et al. |
| 6,546,785 B1 | 4/2003 | Discenzo |

FOREIGN PATENT DOCUMENTS

| | | | |
|---|---|---|---|
| WO | WO 2003/098161 A2 | 11/2003 | |

OTHER PUBLICATIONS

Irion et al., "Oil-Quality Prediction and Oil-Level Detection with the TEMIC QLT-Sensor Leads to Variable Maintenance Intervals", SAE Paper No. 970847, pp. 105-110.*

Ernest Frank, "Electrical Measurement Analysis", 1959, pp. 132-157, McGraw-Hill Book Company.

Van Bramer, S.E., "Notes on Statistics", Mar. 8, 1995.

\* cited by examiner

SYSTEM AND METHOD FOR DYNAMIC LUBRICATION ADJUSTMENT FOR A LUBRICATION ANALYSIS SYSTEM

CROSS-REFERENCE TO RELATED APPLICATIONS

This application is a continuation of U.S. patent application Ser. No. 10/370,866, filed Feb. 20, 2003 now U.S. Pat. No. 6,877,360, entitled, "SYSTEM AND METHOD FOR DYNAMIC LUBRICATION ADJUSTMENT FOR A LUBRICATION ANALYSIS SYSTEM," which is a continuation of U.S. patent application Ser. No. 10/036,154, filed Oct. 22, 2001, now U.S. Pat. No. 6,546,785, entitled, "SYSTEM AND METHOD FOR DYNAMIC LUBRICATION ADJUSTMENT FOR A LUBRICATION ANALYSIS SYSTEM," which is a Continuation-in-Part of U.S. patent application Ser. No. 09/257,680, filed Feb. 25, 1999, now U.S. Pat. No. 6,324,899, entitled, "BEARING SENSOR INTEGRATION FOR A LUBRICATION ANALYSIS SYSTEM," which is a Continuation-in-Part of U.S. patent application Ser. No. 09/054,117, filed Apr. 2, 1998, now U.S. Pat. No. 6,023,961, entitled, "MICRO VISCOSITY SENSOR AND LUBRICATION ANALYSIS SYSTEM EMPLOYING THE SAME." The entireties of the aforementioned applications are incorporated herein by reference.

TECHNICAL FIELD

The present invention generally relates to a lubrication analysis system and more particularly to dynamic lubrication adjustment for such a system.

BACKGROUND OF THE INVENTION

Dynamoelectric machines such as motors and generators are widely employed in industrial and commercial facilities. Many facilities operate several hundred or even thousands of such machines concurrently and these machines are often integral components of large interdependent processes. Accordingly, the machines are each depended upon for prolonged consistent operation whereby it is extremely advantageous to provide reliable failure prediction information. Of particular relevance in the present invention are bearing-related failures and, more particularly, failures related to lubrication problems in antifriction bearings. Diagnostic studies have consistently reflected that bearing-related failures are a substantial cause (about 42% of reported failures) of motor failures.

An antifriction bearing is designed to constrain rotary or linear motion while minimizing wear and other losses such as friction. Examples of this type of bearing are sleeve bearings, hydrodynamic bearings, and rolling element bearings. The most prevalent bearing type found on medium and low horsepower (e.g. fractional to 500 hp) motors are rolling element bearings such as ball bearings. To this end, typical antifriction bearings normally include a bearing housing defining an annular chamber and a plurality of rolling elements retained within the chamber. The bearing housing typically includes two annular components known as raceways, and more particularly an outer raceway and an inner raceway having interior surfaces which form the radial walls of the bearing chamber. (In the context of the present invention, "interior" corresponds to the relation of the surface relative to the chamber.) For example, the outer raceway may be mounted to a machine (e.g., a motor) and is intended to remain stationary relative thereto, while the inner raceway supports a rotating member (e.g., the motor's rotor or shaft).

The rolling elements may be either balls or rollers and the bearing may include one or more rows of such rolling elements. A cage is usually provided to retain the rolling elements in their correct relative positions so that they do not touch one another and to provide some guidance for the rolling elements. Also a lubricating fluid, such as oil or grease, is contained within the bearing chamber to reduce the friction between the components and also assist in the dissipation of heat. The top and bottom (or axial) ends of the chamber are sealed by the mounting structure or by sealing covers to maintain the lubricating fluid within the bearing chamber and/or keep dirt or other contaminants out. An antifriction bearing may include a circulating system to inject and/or drain lubricating fluid into the bearing chamber.

The loss of lubricating effectiveness will result in accelerated wear of the bearing elements, additional heat generation due to frictional effects, higher levels of vibration and potential impact loading due to metal-to-metal contact, and accelerated degradation of lubricant health due to higher levels of temperature, metal particulate contamination, and higher loading/shear levels.

Needless to say, the health of lubrication is a significant factor in the overall operation of an antifriction bearing. Accordingly, it is essential that the lubrication of an antifriction bearing be properly provided, protected, and maintained. Initially, it is important that the correct lubricating fluid be provided for the antifriction bearing. Also, it is critical that an adequate amount of lubricating fluid be maintained in the bearing. Likewise, it is crucial that contaminants (such as water, rust, and other contaminations) not contaminate the lubricating fluid. Moreover, when the lubricating fluid is continuously exposed to elevated temperatures, accelerated speeds, high stress/loads, and an oxidizing environment, the lubricating fluid will inevitably deteriorate and lose its lubricating effectiveness.

Also, when machinery is re-lubricated by applying additional lubricant, the addition of a different, incompatible lubricant will result in considerably diminished lubricating effectiveness. The result may be accelerated bearing wear beyond what would occur if no additional lube was added. The loss of bearing lubricant due to a seal failure is important to detect to prevent accelerated bearing wear and to avoid a dry running condition. It is also important to detect the loss of bearing lubricant in critical manufacturing processes such as pharmaceutical, medical products, and food products manufacturing. Loss of lubricant could result in a contaminated product or worse a contaminated product which remains undetected before reaching the consumer.

Lubrication-related problems tend to be insidious. There is often only a minor degradation of the lubricating fluid at the beginning. However, continued operation of the machine results in even greater heat generation and accelerated degradation of the lubricating fluid. Left untreated, the bearing will eventually fail leading to substantial machinery damage. In short, the continued operation of a degraded bearing will generally destroy machinery beyond just the bearing and repair costs can be extremely high, not to mention the catastrophic and potentially unsafe conditions such a failure creates. Unfortunately, many lubrication-related problems are only recognized after irreparable destruction has occurred to not only the bearing, but the machine itself. For example, some lubricant problems eventually result in a bearing seizing up and the continued rotary motion destroying the rotating shaft or the bearing mounting. Alternatively uncontrolled vibration could occur, resulting in destruction of machinery and buildings.

The previous discussion presented bearings and lubrication issues from the standpoint of motor-mounted bearings. The problems identified and the need for lubricant health information applies to bearings found in a wide range of machinery, including machinery connected to a motor (driven equipment), land-based vehicles, shipboard systems and aircraft systems. This includes bearings in internal combustion engines, engine accessories, gears and gear systems, wheels, linear slides, conveyors, rollers, and pillow blocks for example.

Accordingly, an early diagnosis and cure of lubrication-related problems can be extremely beneficial in reducing machine down-time, repair cost, inconvenience, and even hazardous situations. For this reason, conservative lubricant changing schedules (where the lubricating fluid is changed well before any degradation is expected to occur) are sometimes well worth what may be viewed as wasted labor and wasted lubricating fluid and un-necessary machinery down-time if needed. Other times, however, the cost and labor associated with replacing adequate functioning lubricating fluid cannot be justified. Additionally, the more frequent the changes, the higher the possibility that the wrong lubricating fluid will be provided and/or other changing mistakes will be made such as over lubricating equipment. More importantly, each lubrication situation seems to be relatively unique in view of the almost countless factors that can contribute to lubrication degradation. As such, in many situations, a lubricating fluid will reach at least the initial stages of breakdown or contamination well before even a conservative scheduled change.

The potential damage associated with inadequate bearing lubrication and the uniqueness of each lubrication situation has led many industries to adopt programs of periodic monitoring and analyzing of the lubricating fluid. In some programs, for example, the condition of the lubrication is determined by measuring a dielectric constant change in the lubricating fluid. In other programs, for example, the condition of the lubrication is instead determined by recording historical thermal readings. Unfortunately, these programs measure only a single parameter, such as temperature over time, require the use of the same lubricating fluid, and/or assume no machinery malfunctions between measurements. Furthermore, extensive lubrication monitoring and analysis techniques are not performed in situ and typically involve extracting a sample of the lubricating fluid and then analyzing this sample using laboratory equipment. As such, these sampling techniques only provide a narrow, periodic view of lubrication quality and/or health whereby accurate lubrication health assessment and lifetime prediction is virtually impossible to achieve. Moreover, the manpower required to extract the lubricant samples necessarily limits the frequency of sampling, not to mention the introduction of human error into the extraction process. In some situations, lubricating oil may be extracted from machinery and put in glass bottles in front of a light source. A visual inspection is made after the material had settled.

In view of the above, analysis of fluids including lubricating fluids is an extremely important area and rapidly growing in importance (e.g., machinery, safety, environmental, and so forth). There is a significant expenditure of dollars for outside lab analysis of fluids and also for staff time and for on-site factory-resident labs. Also, there are a variety of lube analysis techniques that include lab analysis methods (e.g., titration methods) and sensor-based methods (e.g., pH sensors, $H_2O$ sensors, dielectric sensors). Lab analysis techniques, however, are limited due to the time delay before a lube analysis is available, possible contamination of the samples extracted for analysis, the cost required for the analysis, and the difficulty in determining what corrective action is needed and when.

Although lube sensors offer improvement over how machines were maintained in the past, other problems are still encountered. For example, maintenance engineers generally still must go to the machinery and lubricate equipment periodically based on equipment usage and lubrication health. In addition, many pieces of rotating machinery and associated grease fittings are difficult to reach, whereby other problems relate to accelerated failure due to over lubricating equipment and by employing the wrong type of lubrication, for example.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates to a system and methodology to facilitate analysis, diagnosis and maintenance of lubricating fluids and to mitigate costs associated therewith. A low-cost fluid sensor for embedded applications can be applied to a plurality of diverse applications and can be employed to dynamically control quantitative and qualitative aspects of the fluids in order to mitigate effects such as degradation, depletion, and oxidation, for example. As an example of the diversity provided by the present invention, embedded applications can include automotive (e.g., engine, drive train, cooling systems, fuels), industrial machinery (e.g., gears, bearings, cutting fluids, hydraulic fluids), aircraft, food processing (e.g., oils, preservatives), and medical (e.g., in-vivo applications, medicines, other bio-fluids).

In accordance with one aspect of the present invention, a multifunctional and modular system is provided that includes one or more sensors to monitor fluids such as lubricants, hydraulics, oils and greases, for example. Information received by the sensors is then processed to determine if the fluids are functioning according to predetermined ranges of suitable fluid operating parameters. If it is determined that one or more parameters are outside of the predetermined operating ranges, one or more actuators or valves are provided that can dynamically adjust one or more of the fluid parameters—even during operation of related machinery or other equipment.

Dynamic adjustments to fluids can include adjusting fluid levels and chemical deficiencies in the fluids along with adjusting characteristics of the fluid based upon environmental considerations (e.g., making fluid adjustments according to duty cycle, load, and temperature of associated equipment). The sensor information can also be provided to external control systems to adjust operating characteristics in accordance with the current detected state of the fluids. For example, if a fluid were determined to be running hotter because of depletion, the sensor information can be employed to adjust the speed or torque of a controller and related equipment in order to extend the life of the lubricant.

Another aspect of the present invention includes utilizing the sensor information collected above to further enhance diagnostic and prognostic aspects of the present invention. This can include providing data quality metrics along with sensor information to indicate not only the operating characteristics of fluids but also to indicate information that relates to the health or status of the sensor reporting the fluid information. In this manner, equipment can be better maintained since information is provided according to the current operating status of the fluids indicating when corrective actions are needed. To further facilitate the process, predictive information is provided relating to the quality of the components that detect when the corrective actions are needed, thus increasing the overall confidence and accuracy of the system.

According to another aspect of the present invention, lubricant operating life is extended to further reduce maintenance and costs associated with lubricant replacement. This can be achieved by exciting one or more electrodes via excitation pulses to reduce oxidation present in the lubricants. In addition, other processes can include energizing one or more magnetic or other type structures to facilitate removal of metallic particles that may have accumulated in the lubricant—thus, enhancing operational life of the lubricant. By reducing oxidation and contaminants in the lubricant, effective lubricant lifetime can be extended. Thus, the period required for re-lubricating equipment can be extended and possibly, a lubrication cycle can be eliminated. Consequently, maintenance costs and equipment downtime can be mitigated. Costs can also be saved by deferring re-lubrication until a future plant shutdown and/or scheduled downtime due to the extended life of the lubricant.

Sampling and subsequent restorative operations provided to lubricants can occur as an on-going process, in real time and as part of a closed loop process. Thus, the present invention can incorporate a multi-element lubrication health sensor along with processing and control aspects to not only determine but also to change or affect the overall health of lubricants. Sensors can be implemented in accordance with the present invention for in situ sensing of lubricating fluids such as greases and oils among other fluids, wherein the parameters sensed such as ferrous contamination and oxidation include several critical and prevalent parameters indicating lubrication health. Consequently, the health of lubricants can be characterized in order to indicate remaining lubrication lifetime—in order to specify and control when (in the future) bearings, gear boxes, and/or other systems need to be re-lubricated. Maintenance engineers can then be directed to perform the system maintenance within prescribed times and in some cases less often. This facilitates having the engineer move from a preventive maintenance strategy (e.g., lubricate equipment based on a timed schedule) to a predictive maintenance strategy (e.g., only lubricate equipment when needed to minimize operating costs and extend equipment lifetime), wherein the control aspects of the present invention further mitigate maintenance efforts by automatically sensing and subsequently operating upon lubricant characteristics.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE DRAWINGS

Figure 1:
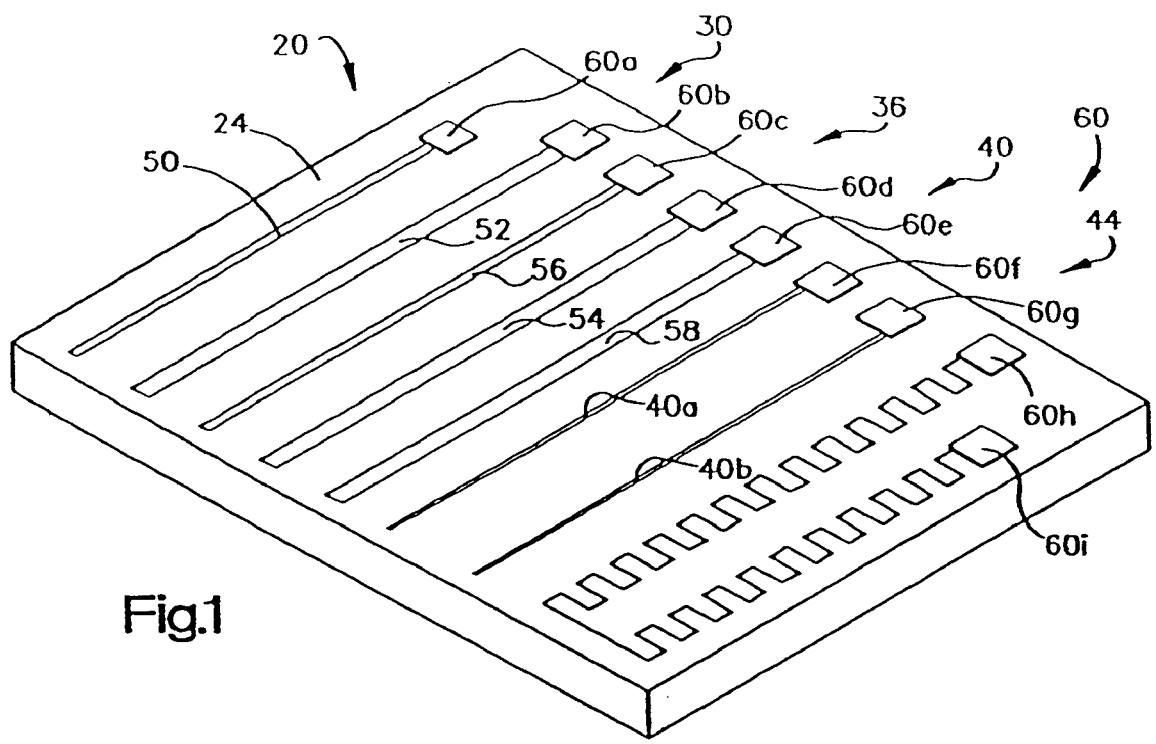
FIG. 1 is a perspective view of an exemplary lubrication sensing device which may be used in a bearing-sensor integration according to the present invention.

Referring now to the drawings in detail, and initially to FIG. 1, an exemplary lubrication sensing device 20 is shown in perspective view. According to the present invention, the lubrication sensing device 20 is integrated into a bearing 22 (FIGS. 4a, 4b and 5–13). This bearing-sensor integration allows in situ lubrication readings to be obtained at a substantially high data sampling rate whereby accurate up-to-date, real-time, continuous data analysis of lubrication health may be provided. In this manner, lubrication maintenance can be scheduled to correspond with the state of the lubrication and/or the processed data can be compiled for trend analysis and forecasting. Lubrication maintenance may be reliably scheduled based on the projected future state of the bearing lubricant. Performing maintenance based on projected future state of the lubricant enables industries to implement effective condition based maintenance programs.

Although the present invention is primarily described in the context of ball bearing systems, it is to be appreciated that the present invention applies to substantially all rolling element bearings (e.g., roller bearings, cylindrical bearings, taper roller bearings, double row ball bearings, sleeve bearings, hydrodynamic bearings). The scope of the present invention as defined by the hereto appended claims is intended to include such bearing applications.

The illustrated lubrication sensing device 20 may be made in accordance with integrated circuit-like fabrication techniques thereby making it possible for the device 20 to have a relatively small geometry, such as a substantially flat square shape having an approximately 4 mm$^2$ area or smaller. Thus, the lubrication sensing device 20 is desirable for bearing-sensor integrations wherein space is at a premium but accuracy, reliability, and sensitivity of measured data are equally as important. Furthermore, the integrated circuit-like fabrication procedures allow the efficient and economic manufacture of large batches and/or high production yields.

The illustrated lubrication sensing device 20 includes a semiconductor base 24, made of silicon or any other suitable material, and a plurality of sensors formed on the base 24. The illustrated sensors include a pH sensor 30 (to determine ionic conditions); a chemical sensor 36 (to determine the presence of chemical contaminants); an electrical conductivity sensor 40 (to determine the presence of metal/water contaminants); and a temperature sensor or detector 44 (to determine temperature and facilitate determining viscosity). The pH sensor 30 includes a reference electrode 50 and a pH electrode 52. The chemical sensor 36 includes a reference electrode 54, a working electrode 56, and a counter electrode 58. The conductivity sensor 40 includes two metal electrodes 40a and 40b. The temperature sensor or detector 44 is essentially a pattern (having known geometric dimensions) formed on the base 24 from a material having an electrical conductivity that varies within the expected range of temperatures. The lubrication sensing device 20 further comprises respective sets of contact pads 60a–60i coupled to the sensors 30, 36, 40 and 44.

Depending on the particular bearing-sensor integration, the illustrated lubrication sensing device 20 may be acceptable and even preferable. However, other lubrication sensing devices are possible with and contemplated by the present invention, and may be more advantageous in certain bearing-sensor integration situations. For example, depending on the desired data collection, certain sensors may be omitted, certain sensors may be repeated, the sensitivities of replicated sensors sealed to cover a wide dynamic range, and/or different types of sensors may be added. For a specific example, a viscosity sensor may be provided that works in conjunction with the temperature sensor 44 to measure the lubricant's viscosity. (A suitable viscosity sensor is shown and described in U.S. Pat. No. 6,023,961, entitled, "MICRO-VISCOSITY SENSOR AND LUBRICATION ANALYSIS SYSTEM EMPLOYING THE SAME.")

Additionally or alternatively, instead of the rigid silicon substrate base 24, the sensors 30, 36, 40 and 44 could be fabricated on a flexible substrate material to accommodate, for instance, in connection with the bearing-sensor integrations shown in FIGS. 4–7. Also, the sensors 30, 36, 40, and 44, could be located on both sides of the rigid or flexible substrate base 24 as might be desirable in, for instance, in the bearing-sensor integration shown in FIG. 9. Alternatively, the sensors 30, 36, 40, and 44 could be "printed" on the bearing 22 itself (e.g., using techniques such as sputtering) to eliminate the need for the substrate 24 as may be advantageous in, for instance, the bearing-sensor integrations shown in FIGS. 4–8. Moreover, as is discussed in more detail below, a processing unit may be incorporated into the lubrication sensing device 20 to perform data acquisition, analyzer functions, communications, afford self diagnosis, establish lubricant health, predict when lubricant service is required, and/or verify feasible operating regimes.

Figure 2:
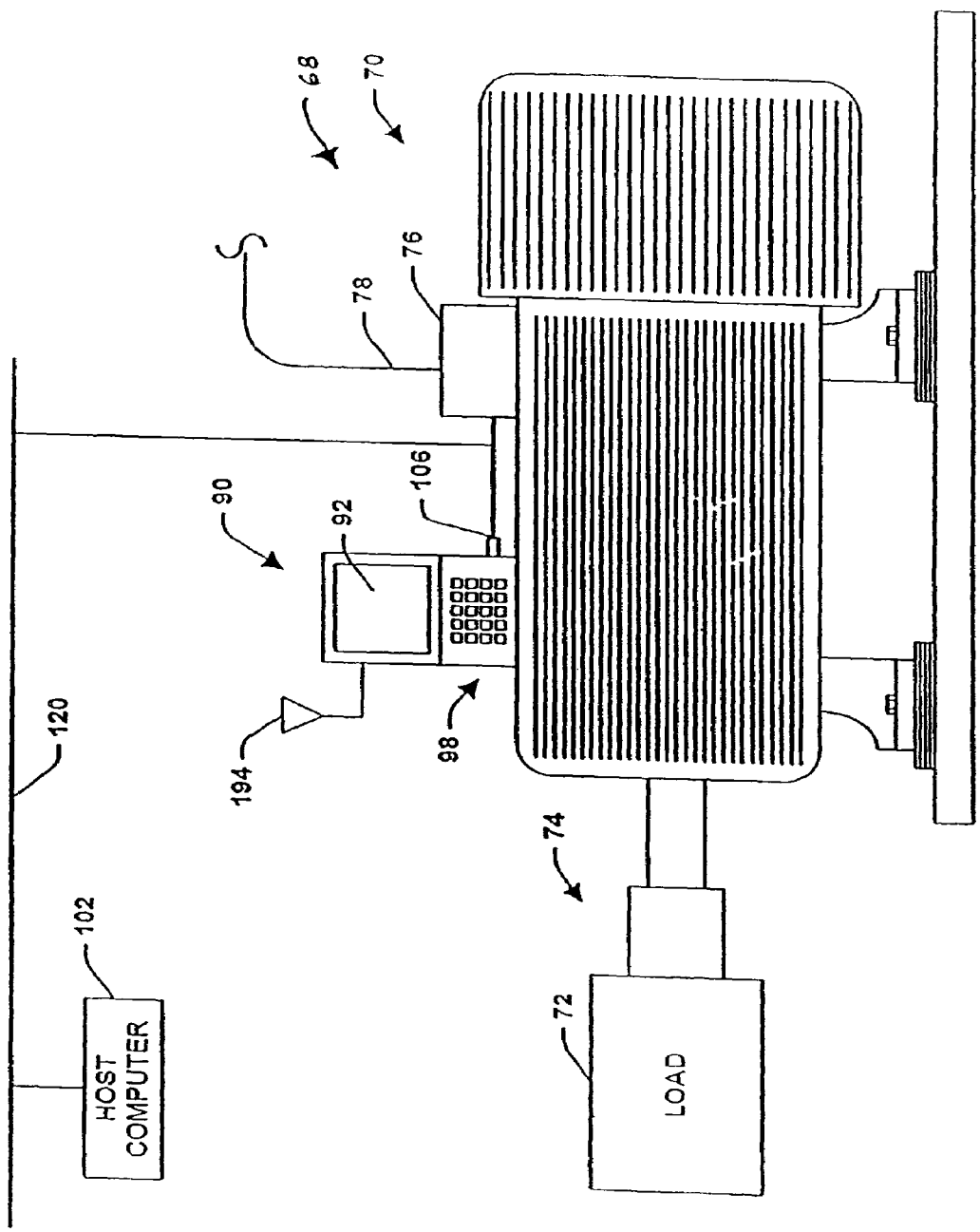
FIG. 2 is an exemplary environment for the bearing-sensor integration according to the present invention is schematically shown.

Referring now additionally to FIG. 2, an exemplary environment for the bearing-sensor integration according to the present invention is schematically shown. In the illustrated example, a lubrication analysis system 68 is used in conjunction with a motor 70. The illustrated motor 70 may be a three-phase AC induction motor that drives a load 72 through a shaft coupling 74 and a junction box 76 is provided to receive and tie power supply lines. In any event, the motor 70 includes one (and probably more) antifriction bearings. For example, two antifriction bearings would typically be used to mount the motor's rotor and/or shaft 74 to the motor end brackets. The system 68 measures, determines, analyzes, monitors, and/or controls the lubrication health of the bearing based on readings received from one or more lubrication sensing devices 20 embedded in the bearings.

The lubrication analysis system 68 includes an analyzer 90 which, in the illustrated embodiment includes a display 92 for displaying lubrication-related information and a keypad 98 for entering data and/or commands. The system 68 further comprises a host computer 102 that makes determinations as to the health of the lubrication, this determination preferably including performing data fusion of the sensed lubricant data (e.g., pH, chemical, conductivity, temperature) to facilitate condensing, combining, trending, forecasting, evaluating and interpreting the sensed data. The analyzer 90 includes a communications port 106 or other interface for receiving information from the lubrication sensing device(s) 20. Once the analyzer 90 (and more particularly its processor 130, introduced below) has processed the lubrication-related data, it is sent to the host computer 102 via a network backbone 120 (which may be hardwired and/or wireless). In this manner, the highly accurate and up-to-date information may be provided regarding the health of the lubrication. Data may be combined from multiple bearings in the host computer 102 and lubrication health and future lubrication requirements may be communicated to plant maintenance, job scheduling, routing, and inventory systems as appropriate.

Figure 3:
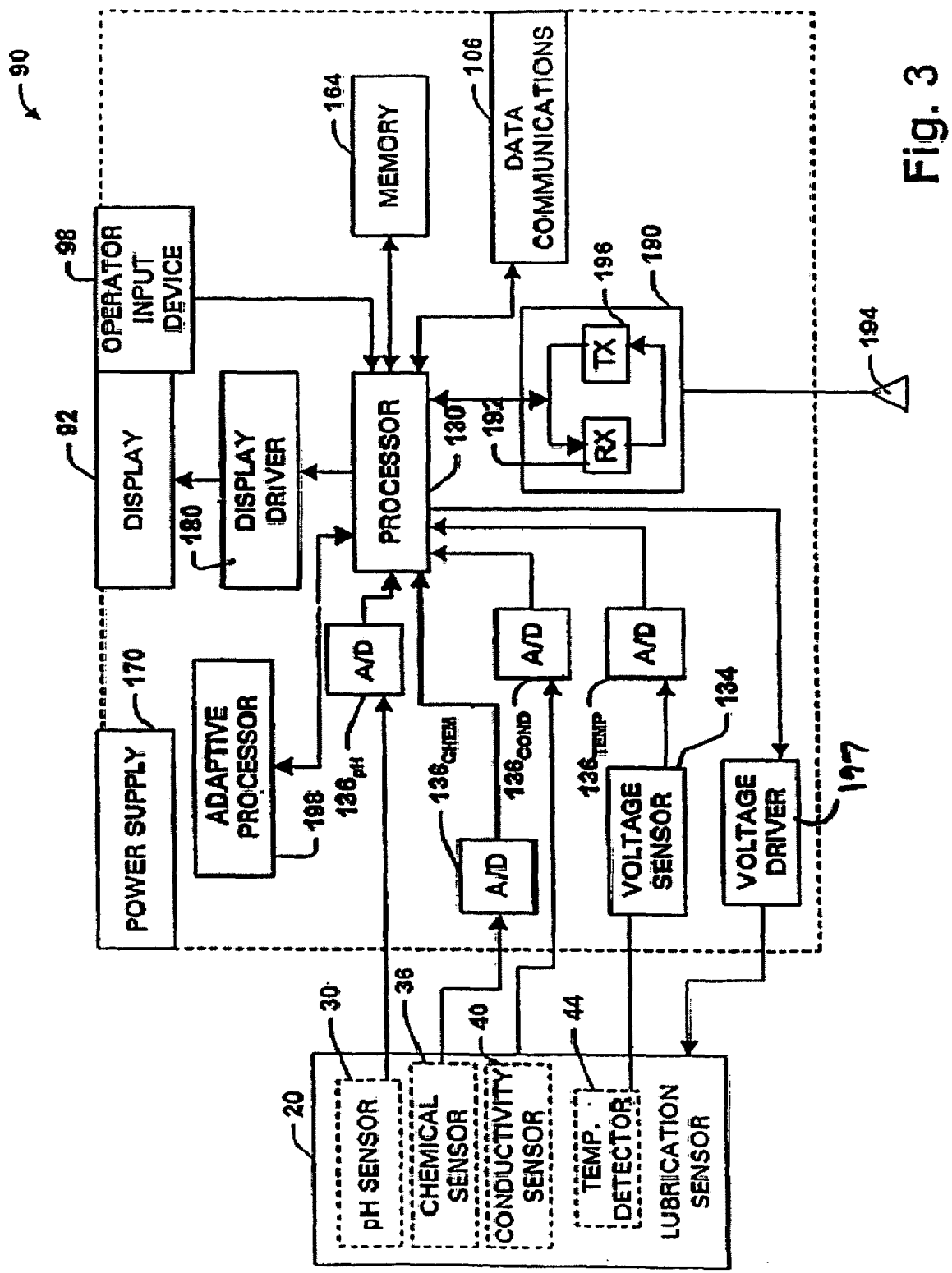
FIG. 3 is a block diagram showing the interaction of the lubrication sensing device and a lubrication analyzer.

Referring now to FIG. 3, further details of the analyzer 90, and its informational connection to the lubrication sensing device 20, are schematically shown. The lubrication analyzer 90 includes a processor 130 which analyzes information received from the lubrication sensing device 20. To this end, the pH sensor 30, the chemical sensor 36, and the conductivity sensor 40 are directly coupled to A/D converters $136_{pH}$, $136_{chem}$, and $136_{cond}$, respectively. The temperature sensor (or detector) 44 is coupled to the A/D converter $136_{temp}$ through a voltage sensor 134. The sensors 30, 36, 40, and 44 are each operatively coupled to the processor 130 via respective A/D converters 136.

The lubrication analyzer 90 includes a memory 164 that stores program code, base-line information (e.g., nominal temperature, acceptable pH, expected electrochemistry, relube information, loading information, duty cycle data, and appropriate viscosity values), machine specific data, acceptable error bounds/deviations, historical lubricant parameter data, and/or recommended corrective action. The lubrication analyzer 90 may also include a power supply 170 (that provides power to the processor 130, sensors and other components), a display driver circuit 180 (that couples the processor to the display 92), RF section 190 (that includes a receiver 192, an antenna 194, a transmitter 196 that transmits and receives signals), a voltage driver 197 (that provides the desired voltage to the lubrication sensing device 20), and/or an adaptive processor 198 (that analyzes the health state of the lubrication).

The lubrication analysis system 68 is designed to provide highly accurate and up-to-date information regarding the health of the lubrication. Additionally, this system will compare known lubricant health with acceptable parameters and projected lubricant aging to establish a recommended maintenance action and when this maintenance must be performed. This information is then communicated to an operator or other computer system as appropriate. Depending on the particular analysis situation and/or the specific bearing-sensor integration, the above-described lubrication analysis system 68 may be acceptable and even advantageous in certain situations. However, other lubrication analysis systems are possible with and contemplated by the present invention, and may even be preferable in certain bearing-sensor integrations according to the present invention.

For example, all of the processing functions (data analysis, lubricant state estimation, health determination, etc.) performed by the host computer 102 in the illustrated embodiment could instead be performed by the processor 130 of the lubrication analyzer 90. In this arrangement, the processed results could be transmitted to a portable computer temporarily tied to the lubrication analyzer 90 and/or transmitted to a remote control computer. Additionally or alternatively, the processed results could be displayed locally on the analyzer display screen 92.

For another example, the lubrication analyzer 90 could be located remotely from the motor 70 or the host computer 102 could carry out substantially all of the lubrication analyzer functions performed by the processor 130 in the illustrated system 68. Another option is to integrate the lubrication analyzer 90 (absent certain components, such as the display 92 and the keypad 98) onto the same base 24 as the lubrication sensing device 20 and/or the bearing 22 to provide for a substantially autonomous lubrication analysis system that performs analyzer functions, affords self diagnosis, and verifies feasible operating regimes.

For a further example, the transmittal of the readings by the sensors 30, 36, 40, and 44 could be modified to fit a particular bearing-sensor integration. In the illustrated lubrication analysis system 68, the analyzer 90 includes the communications port 106 or other interface for receiving information from the lubrication sensing device(s) 20. However, with certain bearing-sensor integrations, such as those shown in FIGS. 6 and 7, wireless sensor technology may be preferred. Additionally or alternatively, in certain bearing-sensor integrations, such as that shown in FIG. 7, an intercommunication between sensors 20 (certain sensing devices 20 relaying information to other sensing devices which then transmit the relayed information to the lubrication analyzer 90) may be the preferred transmittal procedure. To accomplish this wireless technology, low cost integrated silicon RF technology may be coupled to the on-board processor 130. As a further improvement, a magnetic field may be attached to a rotating component of the bearing 22 (such as its inner raceway 210, introduced below), to make the lubrication sensing device 20 self-powering.

For a still further example, the lubrication analysis system 68 could additionally initiate automatic correction procedures. For instance, if the bearing 22 includes a forced lubrication system (such as the system 220 introduced below and shown schematically in FIG. 10), the injection or draining of lubricating fluid could be automatically controlled based on the current lubrication health analysis. Specifically, the detection of low levels of lubricant could automatically trigger the injection of fresh lubricant until an adequate level is reached. The presence of an unacceptable amount of contaminants could trigger a flushing of lubricant to decontaminate the bearing environment. Additionally or alternatively, additives (such as anti-oxidant/desiccant substances) could be automatically introduced to stabilize lubrication performance or even to provide survival lubrication performance during conditions of extreme wear, temperature, duty or mission critical applications. Automatic monitoring and subsequent correction of fluids and other aspects of the present invention are further described in accordance with FIGS. 16 through 19 that are described in more detail below.

By introducing prescribed amounts of additives, lubricant health assessment may be enhanced by monitoring the rate of degradation of the new material. It is also noted that while the lubrication analyzer 90 preferably performs a plurality of functions relating to lubrication health, the processor 130 could be employed for the sole purpose of doing an emergency shut-down of the motor 70 when lubrication conditions approach a critical level.

Referring now to FIGS. 4–15, various bearing-sensor integrations according to the present invention are schematically shown. The bearing 22 is a ball bearing roller bearing of a conventional design and may be viewed as comprising a housing 202 defining a chamber 204 and a plurality of rolling elements 206 (ball bearings in the illustrated embodiment) within the chamber 204. The bearing housing 202 includes an outer raceway 208 and an inner raceway 210 having interior surfaces which form the radial walls of the annular chamber 204. (In the context of the present invention, "interior" corresponds to the relation of the surface relative to the chamber 204.) In the illustrated embodiment, the outer raceway 208 is mounted to the machine (e.g., the motor 70 end bracket) and is intended to remain stationary relative thereto, while the inner raceway 210 supports a rotating member (e.g., the shaft 74). Note, the stationary and rotating elements may be reversed without altering the application of the proposed concept. That is, the inner race may be fixed and the outer race may rotate, for example, as typically occurs in an automobile front wheel bearing.

Figure 9:
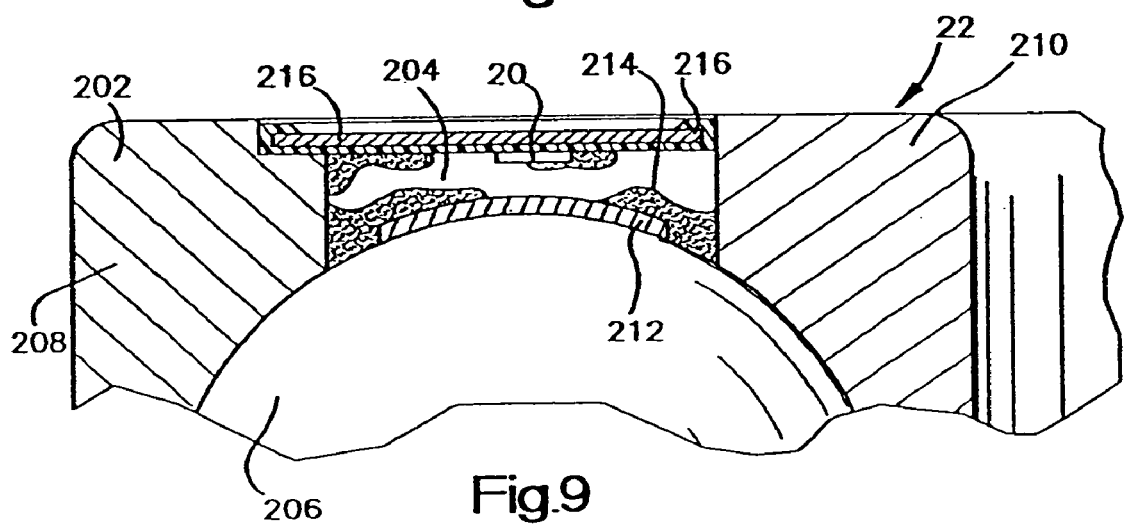

The bearing 22 further includes a cage 212 to retain the rolling elements 206 in their correct relative positions within the chamber 204 and to provide some guidance during the rotation of the inner raceway 210. Also, a lubricating fluid 214, such as oil or grease, is contained within the bearing chamber 204 to reduce the friction between the components and also assist in the dissipation of heat. The top and bottom (or axial) ends of the chamber 204 are sealed by sealing covers (e.g. bearing seals, bearing shields, or the bearing mounting structure) 216 to maintain the lubricating fluid 214 within the bearing chamber 204. (FIG. 9.) The sealing covers 216 may be, for example, washer-shaped members made of felt, leather, plastic, metal, or other suitable materials to seal the annular space between the adjacent axial surfaces of the outer raceway 208 and the inner raceway 210.

Figure 10:
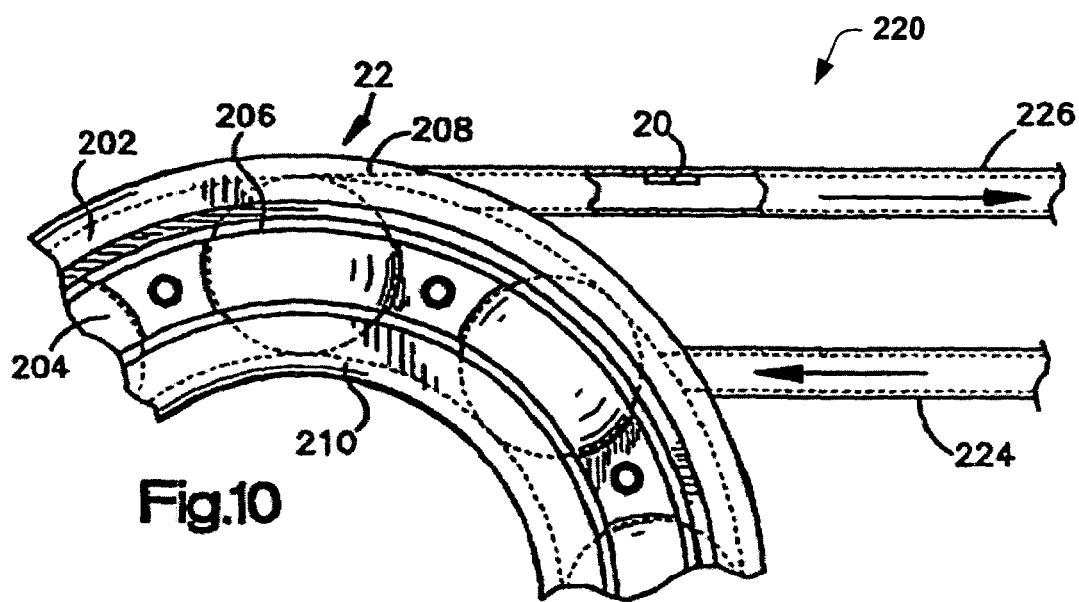

The bearing 22 may include an inlet pipe 224 through which fresh lubricating fluid or additive is pumped into the bearing chamber 204. (FIG. 10.) The inlet pipe 224 may be attached to a pump or pressurized vessel which automatically introduces fresh lubrication fluid 214 into the chamber 204 and an outlet pipe 206 may be provided to automatically drain the lubricating fluid 214 therefrom. (FIG. 10.) The introduction of fresh lube or additive is performed using a small activator integrated with the lube analyzer system. Alternatively, the inlet pipe 224 may be plugged at one end with, for instance, a threaded cap 228 (FIGS. 11 and 12) which may removed for introduction of fresh lubrication fluid. As another alternative, the sensor may be integrated with the grease and/or drain fitting used in conventional re-lubricated bearing systems.

Figure 4A:
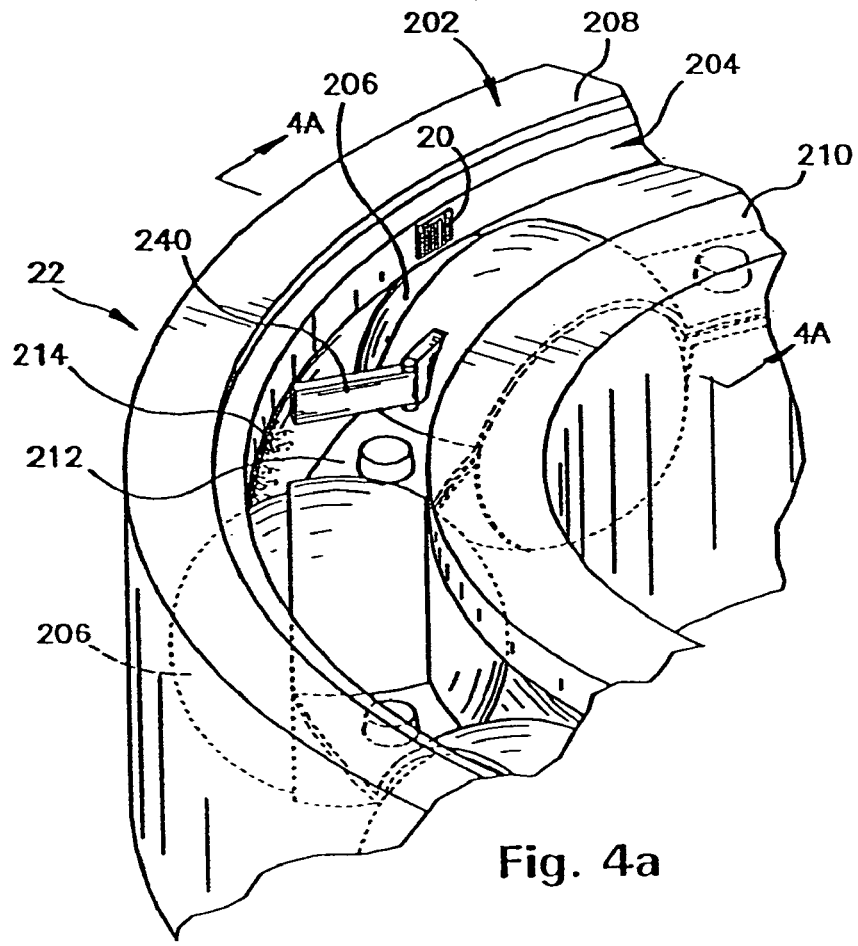
FIGS. 4a, 4b and 5–15 are schematic illustrations of various bearing-sensor integrations according to the present invention.
Figure 4B:
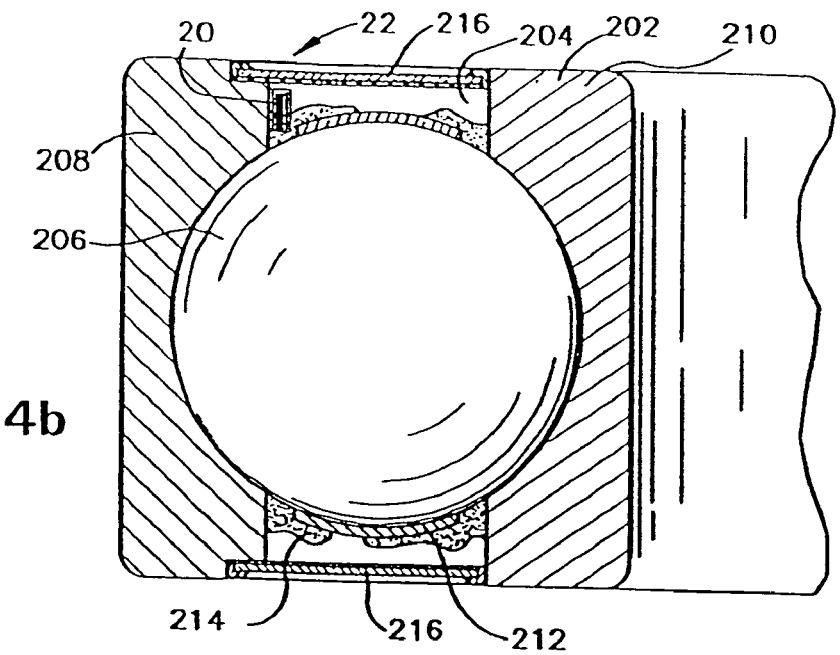

Referring now particularly to FIGS. 4a and 4b, one bearing-sensor integration according to the present invention is shown. In this embodiment, the lubrication sensing device 20 is mounted on an interior surface of the outer raceway 208. Preferably, a small area (about 1 to 4 mm$^2$) is machined in the inner surface of the raceway 208 to provide a mounting location for the sensor 20. The mounting location is preferably in close proximity to the center circular contact path of the ball bearings 206 on the outer raceway 208, but slightly off-center relative thereto to avoid direct contact. Preferably, a wiper arm 240 (such as miniature windshield wiper) has one end pivotally attached to the bearing 22 (and particularly the cage 212) whereby as the cage 212 rotates, unattached portions of the wiper arm 240 are pivoted to transport a changing wedge of the lubricating fluid 214 around the outer raceway 208 and across the sensor 20. It is to be appreciated that a particular embodiment of the invention may have 0 to N (N being an integer) number of wipers. If the analyzer 90 (particularly its processor 130) is incorporated into the lubrication sensing device 20 and/or the bearing 22, this incorporation will provide for a substantially autonomous lubrication analysis system. Also, the non-sensor components (electronics, filtering, processing, and/or communications elements) may be located on the exterior surface of the outer raceway 208 and with vias or solderable contact points extending through the outer raceway 208.

Figure 5:
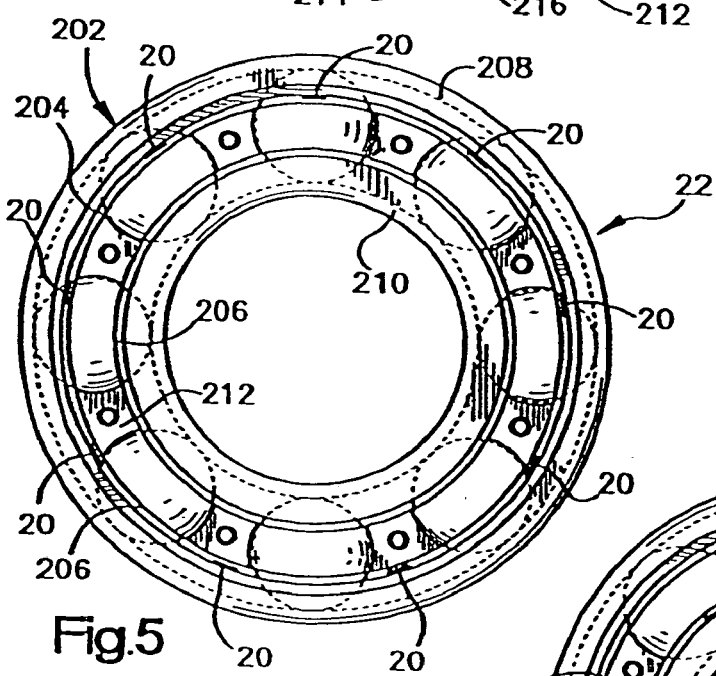

Referring to FIG. 5, a plurality of lubrication sensing devices 20 are mounted on an inner surface of the outer raceway 208. Each of the devices 20 may be mounted in the same manner as the single lubrication sensing device 20 described above in connection with FIG. 4a. Preferably, the sensing devices 20 are equally spaced around the circumference of the outer raceway 208, such as between each rolling element 206. In any event, the use of multiple sensing devices 20 improves analytical accuracy by expanding the range/location of sensor readings, enhances system reliability by redundancy, permits self-diagnosis of the sensors (e.g., a faulty sensor is easily noticed when compared to its sister sensors), allows the correlation of multiple sensor readings over time (to determine, for example, fluid transport time), and essentially guarantees that different samples of the lubricating fluid 214 are being sensed at least by different sensors. From an economic standpoint, the increased expense of a multiple vs. single lubrication sensing device set-up is approximately equal to the cost of the extra sensing devices per se, since shared processing and/or communication for multiple sensing devices is possible.

Figure 6:
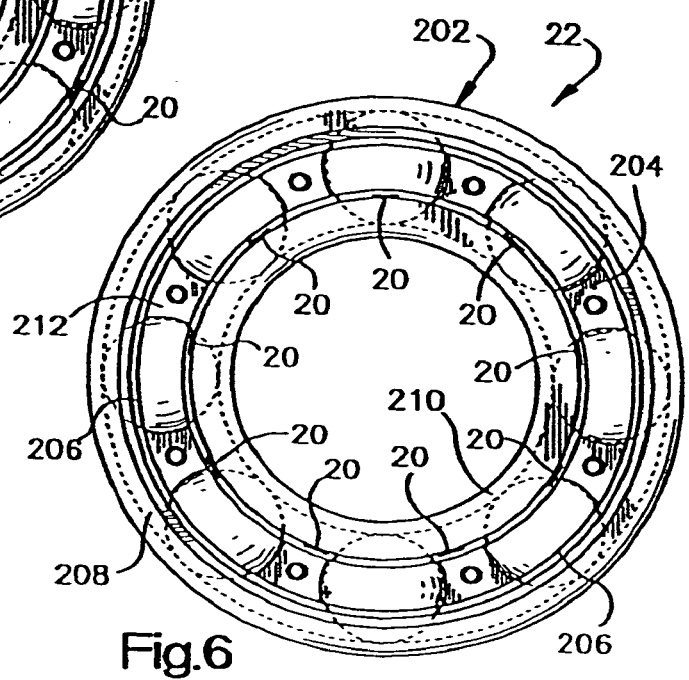

Referring to FIG. 6, a plurality of lubrication sensing devices 20 are mounted on an inner surface of the inner raceway 210. As was explained above, in the illustrated bearing 22, the outer raceway 208 is stationary and the inner raceway 210 rotates during operation of the machine. Accordingly, positioning the sensing devices 20 on the inner rotating raceway 210, as compared to the outer non-rotating raceway 208, may permit a faster sampling of the lubricating fluid 214 and over conditions of changing loading. Preferably wireless sensor technology is used to convey information from the sensors for processing so as to avoid having to run electrical connections from the inner raceway 210 to outside the bearing. (Since the exterior surface of the inner raceway 210 is attached to, for example, the rotating shaft 74, such an electrical connection would require the use of slip-rings if wireless technology was not employed.) Alternatively, the sensing devices 20 mounted on the inner raceway 210 could communicate to other sensing devices within the bearing 22 to permit realtime, continuous monitoring of the elastohydrodynamic film produced by the lubricating fluid 214.

Figure 7:
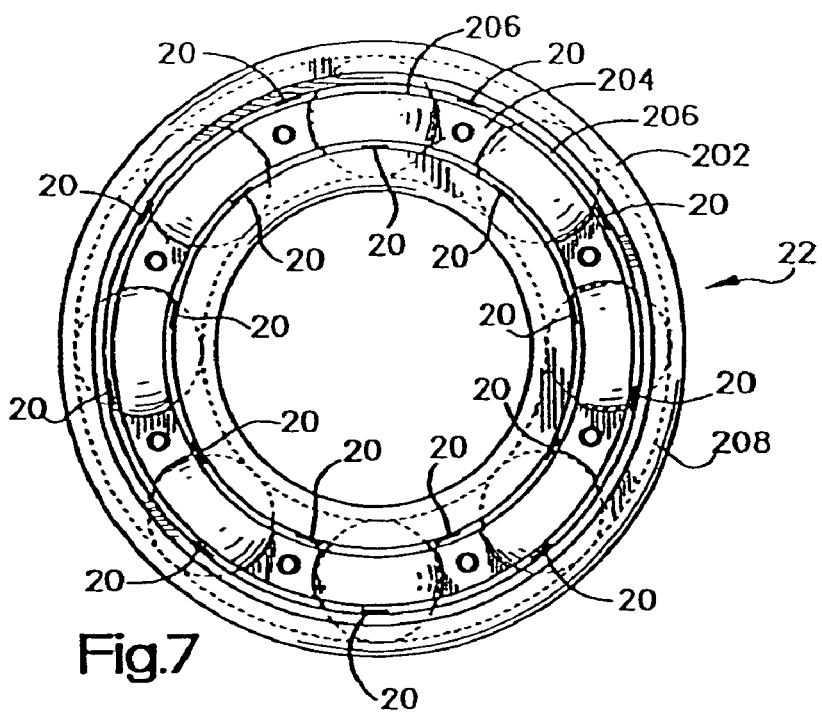

Referring now to FIG. 7, a plurality of lubrication sensing devices 20 are mounted on both the outer raceway 208 and the inner raceway 210. This arrangement would allow the sensing devices 20 on the inner raceway 210 to communicate to the sensing devices 20 on the outer raceway 208. Additionally or alternatively, this arrangement allows the measurement of the electrical and thermal potential between the outer raceway 208 and the inner raceway 210 thereby providing an indication of bearing and lubricant film conductivity and/or the presence of bearing currents.

Figure 8:
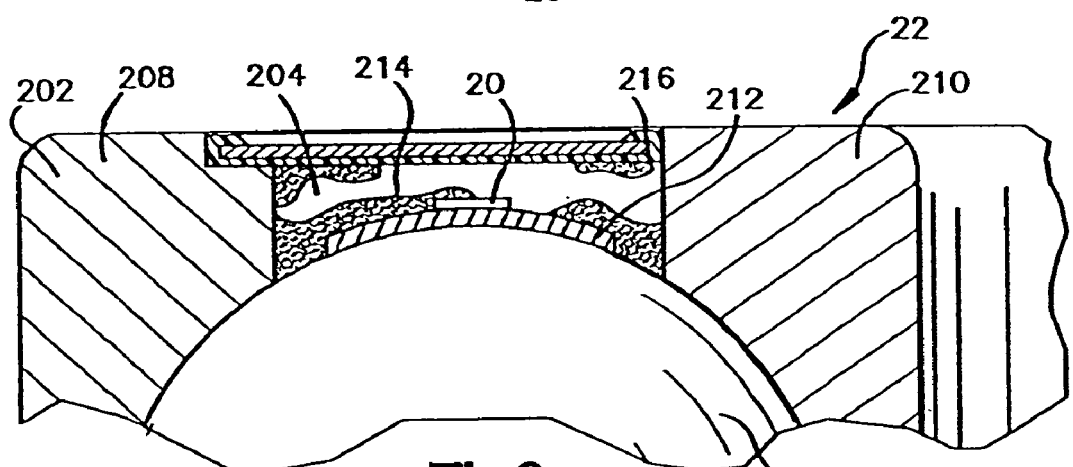

Referring now to FIG. 8, the lubrication sensing device 20 is mounted on the cage 212 of the bearing 22. Mounting the sensing device 20 (or at least the sensors) on the "ball-side" of the cage 212, positions the sensors, in a controlled manner, very close to a moving film of changing lubricant near the surface of the rolling element 206. However, mounting of the sensing device 20 "outside-the ball" side of the cage 212 (as shown) still exposes the sensors to different lubricant locations as the cage 212 traverses around the inner raceway 210 while at the same time minimizing the risk of contact with the adjacent rolling element 206.

Referring now to FIG. 9, the lubrication sensing device 20 is located on the sealing cover 216 of the bearing 22. The sensing device 20 may be attached to a conventional cover or may be incorporated into the cover during its manufacture. In either event, such an arrangement provides for simplified installation and/or replacement of the lubrication sensing device 20. Specifically, an old sealing cover may be removed (usually a relatively inexpensive component as compared to the other components of the bearing, such as the housing 202, the rolling elements 206, and/or the cage 212), and the sealing cover 216 including the lubrication sensing device 20 installed. Also, the lubrication sensing device 20 may be designed (or the sealing cover 216 may include additional instrumentation) to detect and pinpoint lubrication-related problems such as lubrication leakage and/or improperly installed or seated sealing covers. For example, a double-sided sensing device 20 could have sensors on its interior surface to sense pH, chemical conditions, conductivity, temperature and/or viscosity and sensors on its exterior surface for detecting lubricant leakage.

Referring to FIG. 10, the lubrication sensing device 20 may be positioned within the outlet pipe 226 of the circulating system 220. This bearing-sensor integration allows the incorporation of a lubrication analysis system by simplifying re-plumbing the circulation pipes thereby leaving the bearing 22 intact. For similar reasons, this bearing-sensor integration simplifies manufacture, installation, testing and field maintenance procedures of the lubrication sensing device(s) 20. Another significant advantage of this embodiment of the invention is the convenience of operably tying the processed sensor data to the circulation control. Specifically, if the processed sensor data reflects that the lubricating fluid 214 is acceptable, the sample of lubricating fluid 214 may flow back through a bypass pipe (not shown) and introduced back into the bearing chamber 204. However, if the processed sensor data reveals that the lubricating fluid 214 is degraded, the bypass may be closed and the pump activated to inject fresh lubricating fluid into the bearing chamber 204 through the inlet pipe 224 until acceptable sensor readings are received. Alternatively, only additives may be introduced into the lube to accommodate depleted additives (such as anti-oxidants) and re-establish proper lube chemistry.

Figure 11:
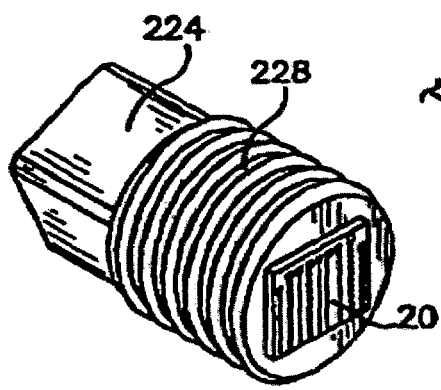
Figure 12:
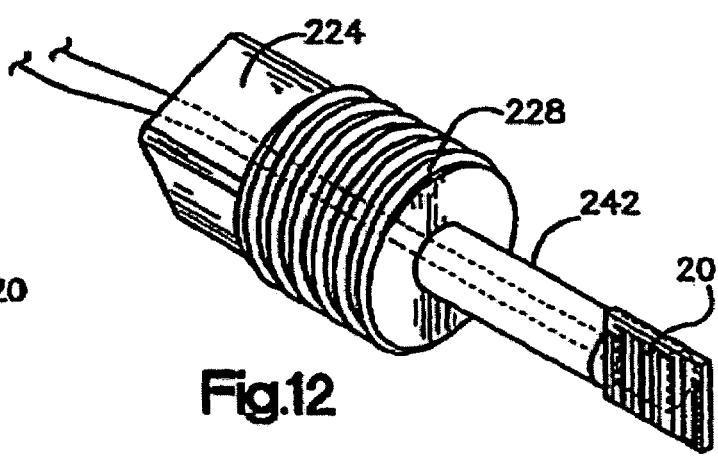

Referring now to FIGS. 11 and 12, the lubrication sensing device 20 is mounted to a cap 228. In the cap-sensor integration shown in FIG. 11, the sensing device 20 is attached directly to the cap 228. In the cap-sensor integration shown in FIG. 12, the sensing device 20 is attached to a probe 242 extending through the cap 228. In either event, such a cap-sensor incorporation provides for simplified installation of the lubrication sensing device 20 by removal of the conventional cap and/or probe and replacement thereof by one including the sensing device 20. Such a cap-sensor integration may be employed in many types of machines employing lubrication and/or fluid reservoirs.

Figure 13:
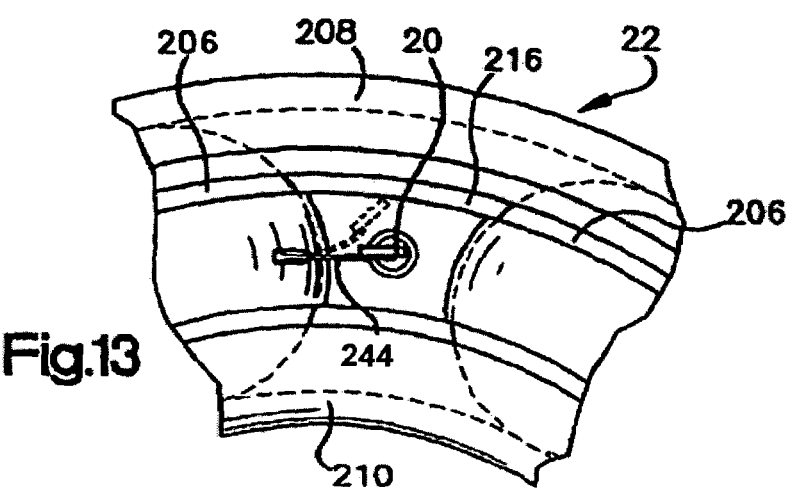

Referring now to FIG. 13, the lubrication sensing device 20 may be mounted on a compliant structure 244 (conceptually like a "rubber policeman") that is geometrically designed to "ride" a moving film surface of lubricant. In this manner, the sensing device 20 (or at least its sensors) may be positioned in close proximity to the moving lubricant film surface (such as adjacent the raceway 208/210 or the cage 212) while at the same time shielding the sensors from direct contact damage. Also, such a bearing-sensor integration allows the distancing of non-sensor electronic elements away from the sensor elements (such as within the compliant structure 244 or within the rigid mounting base).

Figure 14:
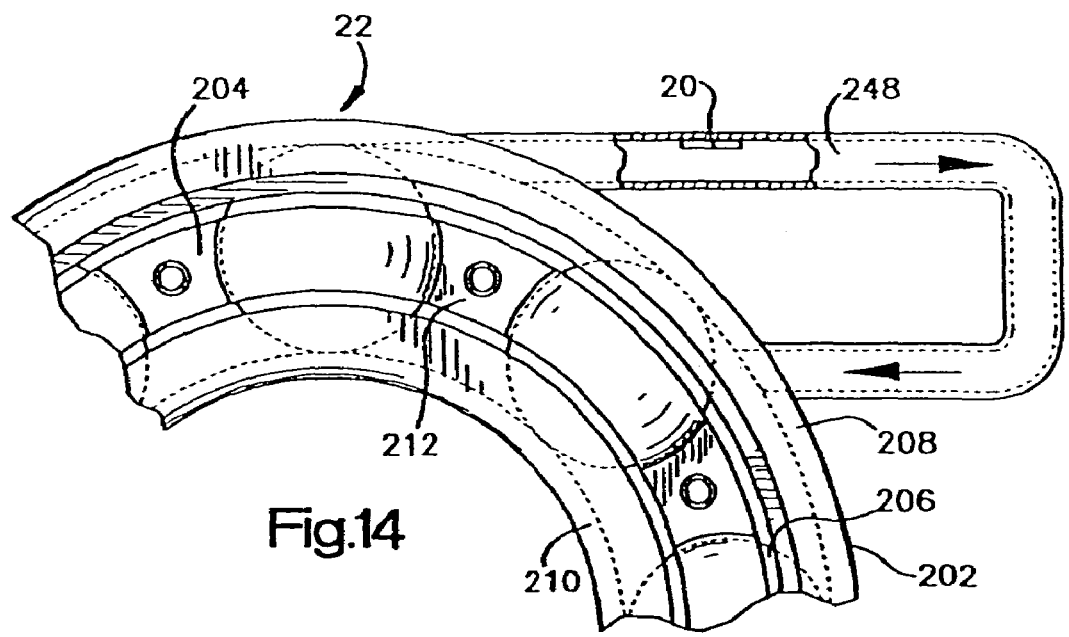

Referring now to FIG. 14, the lubrication sensing device 20 is located within a flowgate 248. The flowgate 248 defines a small bypass channel for diverting a small test or sample amount of lubricating fluid 214 away from the bearing chamber 204 and then reintroducing it back into the bearing chamber 204 once it has flowed past the lubrication sensing device 20. The flowgate 248 is positioned to utilize the moving action of the rolling elements 206 and/or the cage 212 to in effect pump a sample of the lubricating fluid 214 through the bypass channel. This arrangement allows the sensing device 20 be positioned away from the moving components of the bearing 22 (e.g., the rolling elements 206 and the cage 212) while at the same time providing for a continuous exchange of lubricant flowing past the sensing device 20. The bypass channel may be much smaller than shown in FIG. 14 and effectively integrated within the outer race 208 of the bearing.

Figure 15:
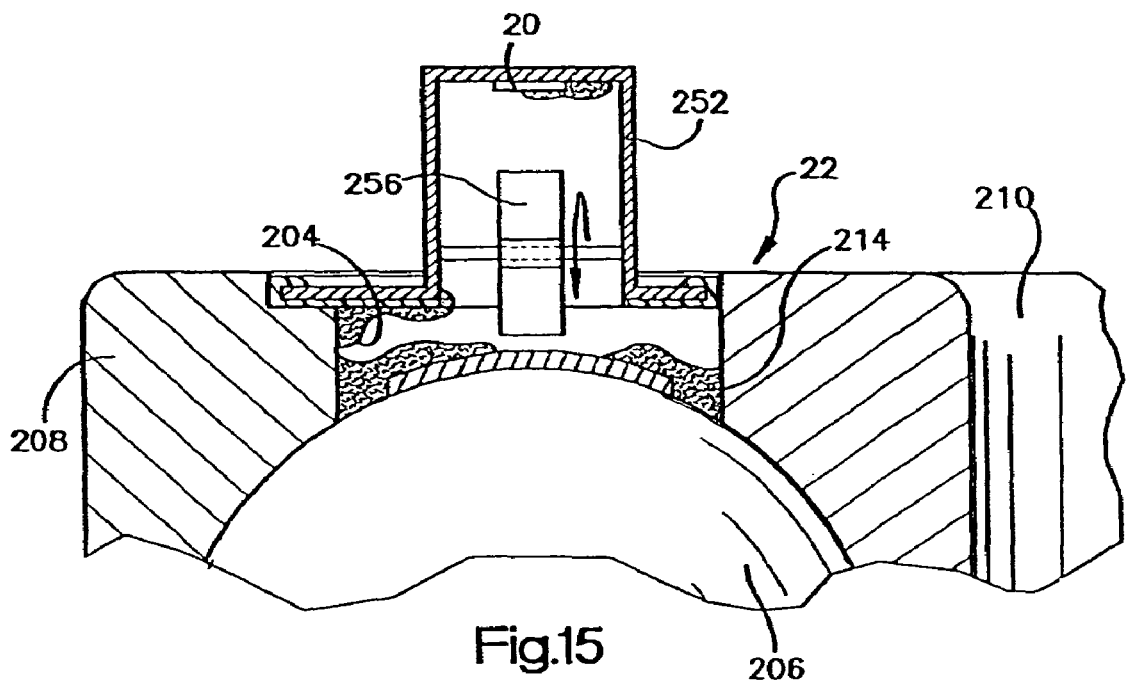

Referring now to FIG. 15, the lubrication sensing device 20 is located within a small reservoir 252 which communicates with, but is positioned outside, the bearing chamber 204. A rotating paddle 256 (essentially a miniature paddlewheel or propeller having a hub rotatably mounted to the bearing and paddles projecting radially outward from the hub) is provided so that it spins as the rolling elements 206 and the cage 212 rotate thereby and/or as the lubricating fluid 214 is circulated thereby. In this manner, the sensing device 20 is constantly presented with untested samples of the lubricating fluid 214 while at the same time the sensing device 20 is physically isolated from the moving bearing components. This bearing-sensor integration may allow a more "rugged" mounting of the sensing device 20, a more precise positioning of the device 20 in relation to the moving lubricating fluid, easier integration of sensing and electronics components, a mechanical base for self-powered operation, and/or simplified integration of the sensor 20 into the bearing 22.

In connection with the bearing-sensor integrations shown in FIGS. 4–15 (and also in connection with any other bearing-sensor integrations possible with and contemplated by the present invention), the reliability and credibility of the processed results depends initially on the sensor readings accurately reflecting the true state of the lubricating fluid 214. Specifically, if the sensors are repeatedly sensing the parameters of only a small static portion of the lubricating fluid 214, rather than the lubricating fluid as a whole, the most advanced and sophisticated processing procedures may not be able to provide an accurate analysis. For this reason, it may be important that untested samples of the lubricating fluid 214 be continuously encountered by the sensing device(s) 20. In certain bearing-sensor integrations, this is accomplished by the use of a plurality of sensing devices 20 (see, e.g., FIGS. 5–7), the positioning of the sensing device(s) 20 on or near a moving component of the bearing 22 (see e.g., FIGS. 6–8), and/or the positioning of the sensing device(s) in locations of force fluid flow (see e.g., FIGS. 10–13).

In addition to the positioning of the sensing device(s), the use of certain supplementary fluid transporting mechanisms may be necessary or desirable. For example, the wiper arm 240 in the bearing-sensor integration shown in FIG. 4a or the paddle 256 in the bearing-sensor integration shown in FIG. 15, may be used to insure that the sensing device(s) 20 are continuously exposed to dynamic samples of the lubricating fluid 214. These transport mechanisms may be duplicated, modified, and/or combined for use in other bearing-sensor integrations. Additionally or alternatively, other actuators may be used to transport untested lubricant over the sensing elements. For example, an array of cilia-like coordinated actuators mounted within the bearing 22 may provide the necessary or desired transport arrangement. Other appropriate transport devices include MEMs valves, pumps, and micro-fluidic devices that could be integrated with the sensing devices 20.

One may now appreciate that the present invention provides an integration of the lubrication sensing device 20 into the bearing 22 so that a substantially high data sampling rate can be obtained and highly accurate, real-time, continuous up-to-date data analysis of lubrication health may be provided. In this manner, lubrication maintenance can be scheduled to correspond precisely with the state of the lubrication and/or the processed data can be compiled for trend analysis and forecasting. The time-based expected rate of lube degradation can be used to predict when re-lubrication or other related maintenance action (e.g. replace worn seals) is required. This provides a solid basis for reliable condition-based maintenance directed at one of the most critical, high-maintenance, and failure-prone components in rotating machinery.

Figure 16:
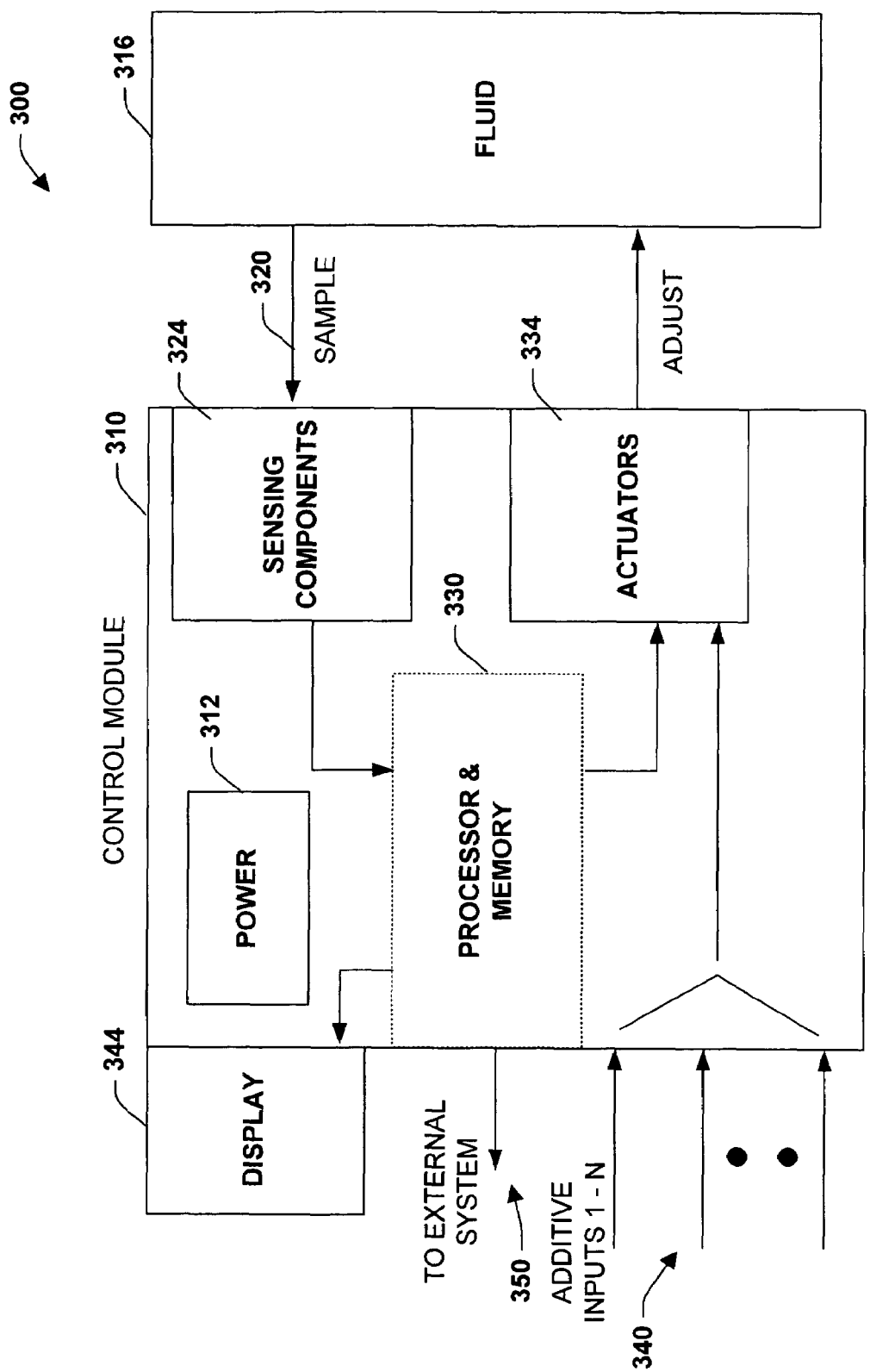
FIG. 16 is schematic block diagram of a closed-loop module to adjust fluid parameters according to an aspect of the present invention.

FIG. 16 illustrates a closed-loop system 300 to dynamically adjust fluid parameters according to an aspect of the present invention. The system 300 can be included as part of a lubrication sensor, device or sensor array described above and can be packaged in a control module 310 (e.g., microelectronic substrate, PCB, Micro Electrical/Mechanical Machine (MEM) structure), wherein a self-contained electrical power source 312 (e.g., battery, piezoelectric power) provides power to components that are contained within the module 310. It is noted that the power source 312 can also be supplied from a source (not shown) external to the control module 310. The control module 310 samples a fluid 316 such as lubricating fluid, hydraulic fluid, oil, grease, fuels, and/or other type compounds, for example, via one or more sample inputs 320 that are sensed by sensing components 324 (e.g., temperature, pressure, viscosity, chemical and so forth) operatively coupled to a processor and memory unit 330. It is also noted that the processing and memory unit 330 can be provided externally from the control unit 310.

The processing and memory unit 330 can be adapted to monitor the chemistry of the lubricating fluid 316 via the sensing components 324 and determine whether additives have been depleted from the fluids such as anti-oxidants. This can be achieved by setting predetermined operating ranges for measured fluid parameter values within the memory portion of the processing unit 330. If a fluid parameter is out of the predetermined range of desired fluid performance as reported by the sensing components 324, the processing unit 330 can dynamically adjust the fluid 316 in accordance with the desired operating range. For example, employing small electrical actuators or MEMs valves 334, the processing unit 330 permits the introduction of additional fluid, such as a lubricant, into an operating device (not shown) that is operative with the fluid 316 to automatically remedy a low lube condition or a chemically depleted lubricant. The additional fluid or agent is provided to the control module 310 through additive inputs one though N (340), wherein N is an integer and dispensed via the actuators 334 as determined by the processing unit 330. In this manner, a closed loop system is provided to maintain the fluid 316 and mitigate costs associated therewith.

The control module 310 can selectively cause specific chemicals to be introduced into the fluid 316 via the actuators 334 and additive inputs 340 to remedy one or more chemical deficiencies (e.g., pH, viscosity). Alternatively, the control module 310 can selectively cause the chemistry of the fluid 316 to change in response to changing environment and duty requirements such as a determined or sensed need for high temperature operation, low temperature operation, and/or heavy load conditions. The additive inputs 340 can include a "tag" or "marker" to permit early detection of a breakdown of a particular chemical and/or presence of a particular contaminant and to facilitate detection via the sensing components 324.

Additives can be formulated to permit real-time replenishment and/or refurbishment of the additives. For example, detergents and other chemical additives can be introduced to the fluid 316 to enable equipment with deteriorated fluid such as a lubricant to survive for a time without a catastrophic failure. In addition to determining and controlling various parameters of the fluid 316, the control module 310 can include a bar graph or other type display 344 driven by the processing unit 330. The display 344 can report such aspects fluid health, remaining lifetime of the fluid before a fluid change is needed, and/or time indications before a filter change is needed, for example.

Other components can also be incorporated within the control module 310. For example, piezoelectric devices (not shown) can be integrated or additional MEMs components added to permit vibration measurements, if desired. Piezoelectric components can also be employed to measure viscosity or density by utilizing structures that are immersed in the fluid 316. Alternatively, piezoelectric components can be employed to generate power 312 for the control module 310. It is to be appreciated that other sensing modalities can also be integrated within the control module 310 such as acoustic wave, magnetic fields with capacitance sensors, optical particle counters and/or optical particle analyzers to further sense or detect the health of the fluid 306. It is noted that the control module 310 can employ sensor fusion to infer and/or determine fluid parameters or other fluid quantities that may not be directly measurable (e.g., inferring ph, viscosity or other fluid parameter from the manner in which fluid responds to control module output or stimulus rather than directly measuring the parameter).

According to another aspect of the present invention, control module information (e.g., sensor data, fluid parameters, range data) can be sent to a control output 350 in order to facilitate dynamic adjustments and control of related machinery. For example, if bearing lube is depleted and running hot, the control output 350 can be operatively coupled to an external controller (not shown) to limit the maximum speed or torque to a lower level which can extend the useful life of the lube before mechanically damaging bearings, gears, or seals. In the case of air conditioning systems as another example, maximum compressor speed or compressor pressure can be limited to reduce the rate of freon degradation and/or freon leakage via the control output 350.

It is noted that a control model (not shown) can be employed (e.g., loop closure around model rather than predetermined parameters described above) that projects and/or predicts the impact of various system changes according to the overall operating environment or other consideration (e.g., load, temperature, power cycling of machine). For example, the model can be configured to predict when a lubricant or fluid should be changed according to sensed and/or inferred conditions of the machinery that utilizes the fluid. It is also noted that the model can be automatically and adaptively updated or enhanced by the control module in order to refine and better predict future conditions for the fluid.

Figure 17:
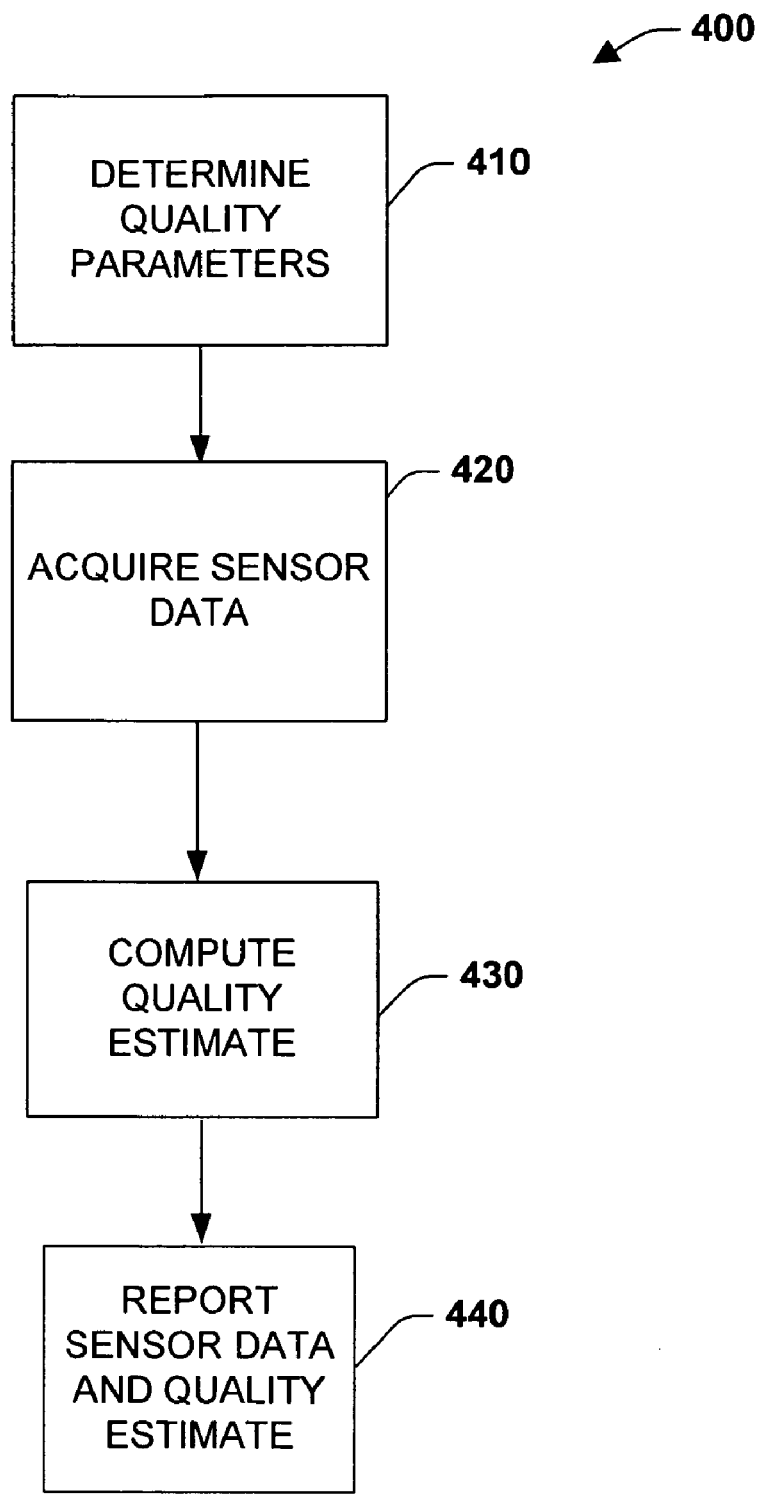
FIG. 17 is a flow diagram of a sensor data and quality collection and reporting process according to an aspect of the present invention.
Figure 19:
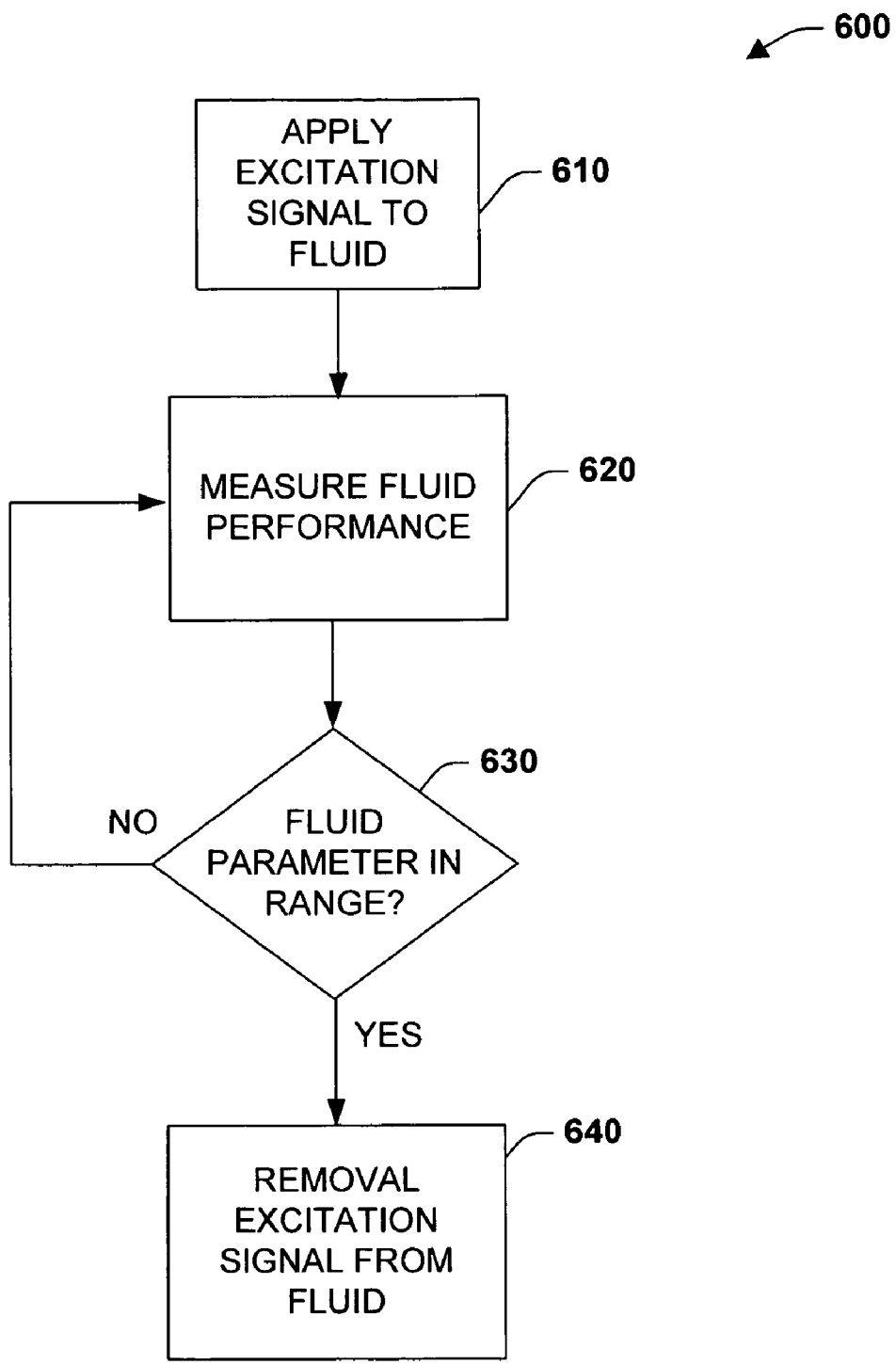
FIG. 19 is a flow diagram of a lubrication control process according to an aspect of the present invention.

FIGS. 17 and 19 illustrate methodologies to facilitate analysis, diagnosis and maintenance of lubricating fluids in accordance with the present invention. While, for purposes of simplicity of explanation, the methodologies are shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

FIG. 17 is a flow diagram of a sensor data and quality collection and reporting process 400 according to an aspect of the present invention. Since multiple sensing components can be employed as described above along with sensor fusion data, useful information regarding the quality and accuracy of data associated with the fluid can be provided. For example, data quality metrics can be readily incorporated into and reported by the control module 310 described above. Proceeding to 410, quality parameters are determined for a fluid. The quality parameters of a lube analysis, for example, can be based on and change according to the time since the last calibration, the degradation of sensor components such as from age, and according to a failure of a sensor component. For example, if a sensor calibration is due or past due, a quality estimate for that parameter can be lowered (e.g., probability or percentage that sensor reliability is less when further away in time from calibration).

At 420, sensor data is acquired (e.g., processor reading fluid sensor component and storing data related thereto). At 430, a quality estimate is computed for the associated sensor based upon the criteria or parameters established at 410. At 440, sensor data is reported along with the associated quality estimate. In this manner, an engineer or system can make more accurate determinations regarding the fluid data as reported by the sensor since reliability of the data is also reported via the associated quality estimate. In this manner, rather than just report an incorrect value, a control module can provide the measured value along with the quality estimate. Alternatively, the control module can provide a corrected sensor value based on historical data, sensor and fluid physics, and/or sensor fusion. Additionally, the control module can provide a "raw"—as read from sensor value, a corrected value, and confidence limits and/or a belief value for the reported sensor data.

Figure 18:
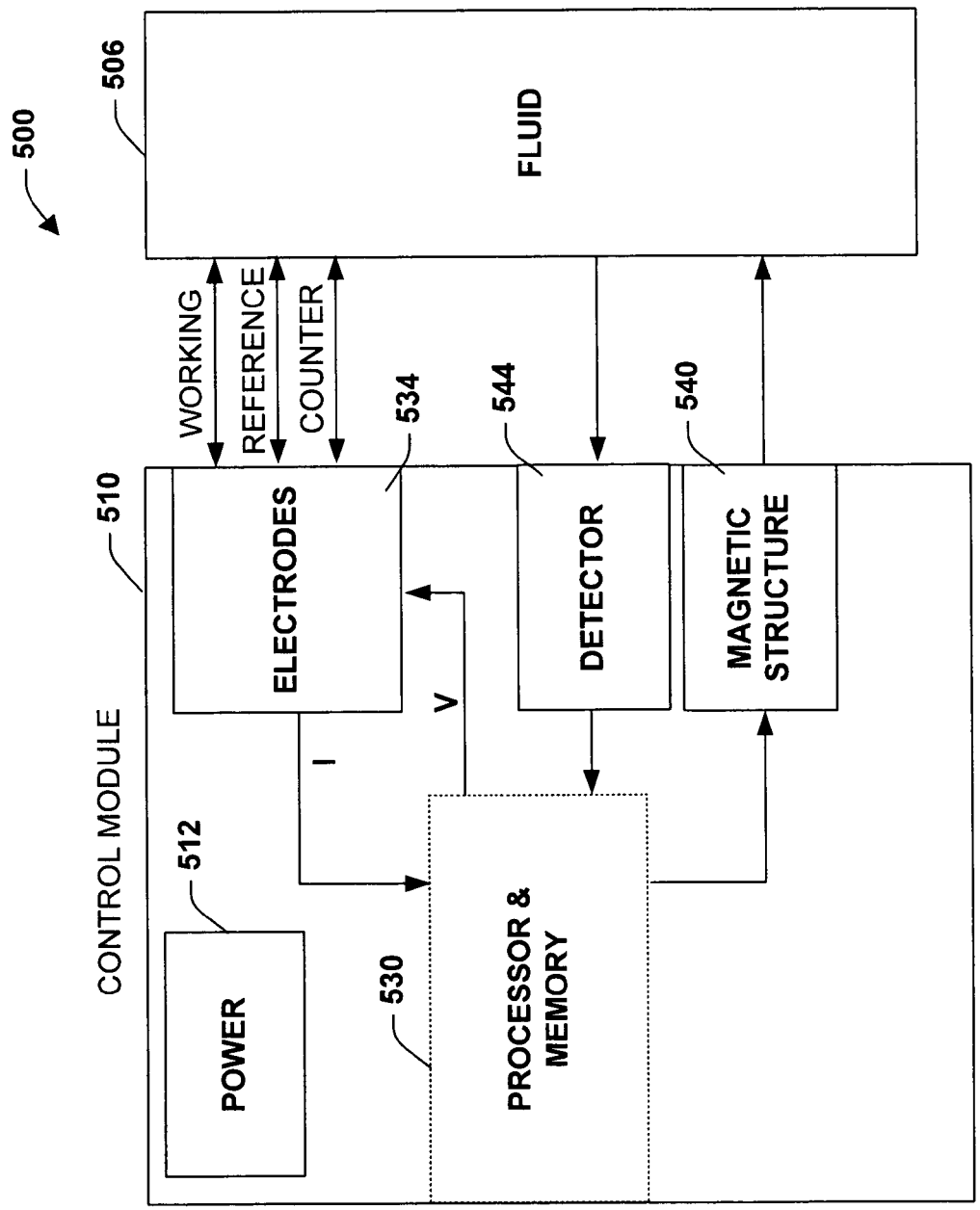
FIG. 18 is schematic block diagram of a closed-loop module to adjust fluid characteristics according to an aspect of the present invention.

FIG. 18 illustrates a closed-loop system 500 to adjust fluid characteristics according to an aspect of the present invention. In this aspect of the present invention, fluid lifetime can be extended via one or more excitation stimuli operative with a fluid 506, such as an equipment lubricant, in order to alter properties of the fluid. The stimuli can be provided via a control module 510 that includes a power source 512, wherein a processing and memory unit 530 is operative to provide control aspects to the module 510 as described below.

Oxidation present in greases and oils can be determined by employing cyclic volta-metric techniques. A multi-electrode component 534 is illustrated including a working electrode, reference electrode, and a counter electrode. It is noted that other combinations or numbers of electrodes can be employed to perform the measurements. For example, a two-electrode system can be utilized to perform cyclic volta-metric techniques. By applying a voltage (V) across the working and reference electrode, a current (I) can be induced in the counter electrode in order to determine such parameters as oxidation in the fluid 506.

The voltage can be cyclically ramped up and down from −5V to +5V to −5V to +5V to −5V, for example, and the current recorded during the voltage excursions. Characteristic peaks observed and analyzed in an I-V curve can be driven by an oxidation and reduction that occurs in the fluid 506 in substantially close proximity to the component electrodes 534. The oxidation reaction is typically not the addition of oxygen to compounds in the fluid 506 but rather the loss of electrons in the compounds. Similarly, a reduction phase of the operation results in a gain of electrons for fluid compounds.

In addition to sensing when the oxidation and reduction has occurred in the fluid 506, the control module 510 can provide an excitation signal via the electrodes 534 to mitigate degenerative aspects of the fluid 506 such as from oxidation—thus, providing loop closure to sense the health and then facilitate restoration of the fluid 506. The excitation signal can be generated for a longer time period and higher voltage (longer/higher—relative to oxidation detection cycles described above) for a reduction phase and followed with a brief, low voltage excitation for a complete reduction cycle. Additional voltage and time spent in the reduction phase is employed to reduce the oxidation present in the fluid compounds such as antioxidants.

Other type electrodes 534 can be fabricated on the control module 510 to provide a larger surface area and support a higher power output for the reduction reaction. It is to be appreciated that an array of such reducing electrodes 534 can be constructed and alternatively, selected portions of the array can be activated if degradation or wear of electrodes occur during the reducing cycle.

Another aspect of the present invention includes fabrication of micro-electronic magnetic structures 540 along with micro-electronic sensors or detectors 544 on the control module 510. The magnetic structures 540 facilitate attracting ferrous metallic particles from the fluid 506, wherein presence of a magnetic field will prevent these particles from flowing freely in the fluid and migrating into rolling elements and associated equipment contact surfaces. A larger structure 540, perhaps outside the path of rolling elements, can serve to mitigate having such metal particles contaminate a raceway, for example. Such attracted materials can also be bound to a sensor electrode via a plating-type operation. The amount of ferrous materials attracted can be measured with any of a number of detectors 544 which include conductivity between several sensor electrodes, plating energy, or capacitive or dielectric strength between several surfaces. It is to be appreciated that oxidation and particle removal aspects of the present invention do not have to be combined into a singular control module but can also be provided as part of separate control module or function.

FIG. 19 is a flow diagram of a lubrication control process 600 according to an aspect of the present invention. This process can be executed by the control modules described above and/or can be implemented according to a control state machine and/or algorithm, for example. Proceeding to 610, an excitation signal is applied to a fluid in order to change or alter the characteristics or performance of the fluid. For example, a voltage can be applied in the form of an extended pulse and/or increased voltage magnitude in order to replenish electrons that have been depleted from the fluid. In another aspect, a magnetic field can be applied as the excitation signal in order to remove contaminants such as ferrous material from the fluid. It is noted that the excitation pulse can also be directed to an actuator or controllable valve, wherein additives are provided to the existing fluid as described above. At 620, fluid parameters are measured in order to determine the effectiveness of the excitation signal applied at 610. For example, current can be measured when applying voltage pulses to determine an amount of oxidation present in the fluid. In the case of ferrous particles, conductivity can be measured between electrodes, measured via plating energy, and/or measured between capacitive surfaces, for example.

At 630, a determination is made whether the fluid measurements of 620 are in range. This can include setting predetermined parameter thresholds and making the determination regarding the fluid based upon the measured parameter being above or below the predetermined threshold. If the measured fluid parameter is in range at 630, the process proceeds to 640 and removes the excitation signal from the fluid or in the case of additives, a valve can be disengaged. If the measured parameter is out of range at 640, the process proceeds back to 620 and performs another fluid measurement. It is noted, that the loop depicted between 620 and 630 can be executed as a background routine, wherein a processor periodically returns, performs the measurement at 620 and makes the determination at 630. In addition, a counter can be set whereby if the measurements taken at 620 are not within range after a predetermined number of readings as indicated by the counter, a control signal can be activated and/or alarm triggered that the fluid is not responding to the excitation signal applied at 610.

What has been described above are preferred aspects of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system that analyzes health of a lubricant in a machine, comprising:
    a component that senses, in situ, a characteristic of the lubricant;
    an analyzer that compares the sensed characteristic of the lubricant with a pre-defined characteristic of the lubricant, wherein the result of the comparison is utilized to determine lubricant health; and
    the analyzer further compares the determined lubricant health with known acceptable parameters and a projected lubricant aging in order to establish a recommended maintenance action and determine when this maintenance must be performed.

2. The system of claim 1, the component is a pH sensor that determines an ionic condition of the sensed lubricant.

3. The system of claim 1, the component is a chemical sensor that determines presence of a chemical contaminant of the lubricant.

4. The system of claim 1, the component is a conductivity sensor to determine presence of at least one of a metal contaminant and a water contaminant of the lubricant.

5. The system of claim 1, the component is a sensor that measures temperature for determining lubricant viscosity.

6. The system of claim 1, further comprising a diagnostic component that dynamically controls a qualitative and/or quantitative aspects of the lubricant based at least in part on the health of the lubricant to reduce at least one of lubricant degradation, depletion and oxidation.

7. The system of claim 1, the lubricant is one of a hydraulic fluid, an oil, and a grease.

8. The system of claim 1, the component further converts the sensed characteristic into a form readable by the analyzer.

9. A system for maintaining the health of a lubricant of a machine, comprising:
   means for sensing a real-time lubricant property;
   means for determining health of the lubricant from the sensed lubricant property;
   means for comparing the determined lubricant health with known acceptable parameters and a projected lubricant aging;
   means for establishing a recommended maintenance action; and
   means for determining when the maintenance must be performed based on the lubricant health data.

* * * * *